(12) United States Patent
Smith

(10) Patent No.: US 6,475,526 B1
(45) Date of Patent: Nov. 5, 2002

(54) ZINC CONTAINING COMPOSITIONS FOR ANTI-VIRAL USE

(76) Inventor: Jeffrey B. Smith, 18915 Detroit Ave., Suite 321, Lakewood, OH (US) 44107

( * ) Notice: Subject to any disclaimer, the term of this patent is extended or adjusted under 35 U.S.C. 154(b) by 0 days.

(21) Appl. No.: 09/874,848

(22) Filed: Jun. 5, 2001

(51) Int. Cl.[7] .................. A61K 31/315; A61K 33/30; A61K 31/045; A61K 31/05; A61K 31/01; A61K 31/60; A61K 47/44

(52) U.S. Cl. .................. 424/642; 424/641; 424/643; 424/744; 514/159; 514/160; 514/161; 514/162; 514/163; 514/164; 514/165; 514/166; 514/266.5; 514/404; 514/412; 514/420; 514/423; 514/494; 514/535; 514/536; 514/537; 514/547; 514/548; 514/557; 514/558; 514/559; 514/567; 514/568; 514/569; 514/570; 514/571; 514/574; 514/626; 514/629; 514/649; 514/650; 514/651; 514/730; 514/731; 514/733; 514/734; 514/735; 514/736; 514/737; 514/738; 514/762; 514/785; 514/786; 514/787; 514/886; 514/887; 514/931; 514/934; 514/937; 514/938; 514/939; 514/944; 514/967; 514/969; 514/970

(58) Field of Search .................. 424/641, 642, 424/643, 744; 514/494, 934, 159–166, 226.5, 404, 412, 420, 423, 535–537, 547, 548, 557–559, 567–571, 574, 626, 629, 649–651, 730, 731, 733–738, 762, 785–787, 886, 887, 931, 937–939, 944, 967, 969, 970

(56) References Cited

U.S. PATENT DOCUMENTS

| | | | |
|---|---|---|---|
| 4,225,614 A | 9/1980 | Hansson | 424/289 |
| 4,407,818 A | 10/1983 | Lionelle et al. | 424/289 |
| 4,465,666 A | 8/1984 | Lukas et al. | 424/145 |
| 4,661,354 A | 4/1987 | Finnerty | 424/145 |
| 4,762,715 A | 8/1988 | Likas et al. | 424/145 |
| 4,911,932 A | * 3/1990 | Chum et al. | 424/642 |
| 5,208,031 A | 5/1993 | Kelly | 424/412 |
| 5,254,549 A | 10/1993 | Gold et al. | 514/247 |
| 5,482,053 A | 1/1996 | Kelly | 128/844 |
| 5,487,893 A | 1/1996 | Vachy | 424/195.1 |
| 5,514,667 A | 5/1996 | Cullis-Hill | 514/54 |
| 5,599,551 A | 2/1997 | Kelly | 424/405 |
| 5,624,675 A | 4/1997 | Kelly | 424/405 |
| 5,767,135 A | 6/1998 | Fernandez-Pol | 514/354 |
| 5,785,054 A | 7/1998 | Kelly | 128/42 |
| 5,804,573 A | 9/1998 | Silver | 514/167 |
| 5,830,456 A | 11/1998 | Cummins | 424/85.7 |
| 5,855,872 A | 1/1999 | Libin | 424/49 |
| 5,965,610 A | * 10/1999 | Modak et al. | 514/494 |
| 6,020,333 A | 2/2000 | Berque | 514/251 |
| 6,060,085 A | 5/2000 | Osborne | 424/484 |
| 6,113,928 A | 9/2000 | Nogueira et al. | 424/401 |
| 6,238,683 B1 | * 5/2001 | Burnett et al. | 424/405 |
| 6,261,574 B1 | * 7/2001 | Costello | 424/400 |

OTHER PUBLICATIONS

Remington's Pharmaceutical Sciences, 17th ed., Mack Publishing Co., Easton (PA), 1985, pp. 1301–1305 & 1580.*

* cited by examiner

*Primary Examiner*—John Pak
(74) *Attorney, Agent, or Firm*—Amin & Turocy, LLP

(57) ABSTRACT

One aspect of the invention relates to anti-viral composition containing at least one zinc compound and at least one phenolic antioxidant (and optionally other ingredients such as at least one analgesic) at least one hydrocarbyl containing compound, and water. Another aspect of the invention relates to a method of treating lesionous symptoms of a viral infection involving applying an effective amount of the zinc containing anti-viral composition to the lesions.

22 Claims, No Drawings

ZINC CONTAINING COMPOSITIONS FOR ANTI-VIRAL USE

FIELD OF THE INVENTION

The present invention generally relates to zinc containing compositions, methods of making zinc containing compositions, methods of using zinc containing compositions, methods of treating viruses, and methods of treating viral induced symptoms.

BACKGROUND OF THE INVENTION

Viral infections effect many people around the globe. Viral infections that cause topical symptoms are particularly troublesome to those afflicted. For example, the herpes simplex virus (HSV) can cause blisters and sores almost anywhere on the skin. These sores usually occur either around the mouth and nose, or on the genitals and buttocks.

Symptoms of HSV infections are in many instances annoying because they periodically reappear. The sores are often painful and unsightly. And with regard to the chronically ill and newborn infants, HSV infection can be serious, although rarely fatal.

There are two general types of HSV; namely, Type 1 and Type 2. The Type 1 virus typically causes cold sores. Type 1 infections frequently occur during infancy or childhood. Infection results from close contact with infected people. The virus can be transmitted by kissing, sharing eating utensils, or even by sharing towels. The resultant sores most commonly affect the lips, mouth, nose, chin or cheeks and occur shortly after exposure. In many instances, infected persons may barely notice any symptoms or need medical attention for relief of pain.

The Type 2 virus typically causes genital sores. Most people get Type 2 infections following sexual contact with an infected person. Various estimates indicate that the virus affects anywhere between 10 and 40 million people in the United States (up to 25% of all sexually active adults in the United States) and up to 400 million people world wide.

With either type of herpes simplex virus, a new lesion can be spread by merely touching an unaffected part of the body after touching a herpes lesion.

Herpes Simplex Virus Type 1, often referred to as fever blisters or cold sores, are tiny, clear, fluid-filled blisters that most often occur on the face. Less frequently, Type 1 infections occur in the genital area. Type 1 may also develop in wounds on the skin.

Herpes Simplex Virus Type 2 usually results in sores on the buttocks, penis, vagina or cervix, two to twenty days after contact with an infected person. Sexual intercourse is the most frequent means of virus transfer. Both primary and repeat attacks can cause problems including: minor rash, itching, painful sores, fever, aching muscles and a burning sensation during urination. While HSV Type 2 may occur in locations other than the genital area, it is usually found below the waist.

As with Type 1, the sites and frequency of repeated bouts of symptoms from Type 2 vary. After the initial attack, the virus moves to nerve cells and remains there until set off again by any one of: a menstrual period, fever, physical contact, stress, or the like. The appearance of HSV is often so typical that no further testing is necessary to confirm an HSV infection.

At the present time, there is no vaccine that prevents this disease from occurring. Oral anti-viral medications such as acyclovir, famcyclovir, or valacyclovir are available to treat herpes infections. These medications can be used to treat an outbreak or can be used for suppressing herpes recurrences. Lower doses may be helpful in reducing the number of herpes attacks in people with frequent outbreaks. However, improved medications are desired, as acyclovir resistant strains of herpes have evolved.

Prevention of this disease, which is contagious before and during an outbreak, is therefore important. It is known that kissing someone while having a fever blister or having sex with one having an outbreak of genital herpes likely leads to transmission of the virus. However, herpes can be transferred if there is no sore. That is, herpes can be transmitted in the absence of lesions. Some estimates indicate that over 80% of all genital herpes is transmitted when there are no visible sores on the skin and no symptoms. The explanation is most likely due to the presence of HSV on the genital skin in the absence of lesions or symptoms. This phenomenon is labeled "asymptomatic viral shedding". Persons who never recall having an outbreak of genital herpes, but who test positive for antibodies to herpes, are believed to "shed" the virus occasionally from lips or genital skin.

Persons who take acyclovir daily often have reduced amounts of the virus in the absence of symptoms or lesions. While there are no known cures for herpes, clinical studies are now ongoing to attempt to reduce or possibly eliminate outbreaks. There is a need to mitigate the effects of herpes.

SUMMARY OF THE INVENTION

The present invention provides anti-viral compositions and methods to mitigate the effects of viral infections. The anti-viral compositions contain active ingredients, such as a zinc containing compound and a phenolic antioxidant, that reduce and/or prevent lesions (and other skin disorders) associated with viral infections, and/or mitigate the transmission of viruses. The anti-viral compositions may be topically applied to areas of concern on an infected subject, such as on the skin and/or mucous membranes. In addition to the zinc containing compound and phenolic antioxidant, the anti-viral compositions optionally contain an analgesic and a vehicle or carrier to deliver at least the zinc containing compound and phenolic antioxidant to the skin and/or mucous membranes of an infected subject.

DETAILED DESCRIPTION OF THE INVENTION

The present invention relates to zinc containing compositions that have anti-viral uses. Anti-viral uses include the ability to reduce or stop the replication of virus, the ability to reduce or eliminate the symptoms caused by the viruses, and/or the ability to inactivate or reduce the activity of the viruses. The zinc containing compositions may also be used to simply treat the symptoms caused by viruses, especially to treat topically skin manifesting symptoms (such as lesions, pimples, blisters, redness, and the like) and to treat mucous membrane manifesting symptoms.

Pain or unusual tenderness of the skin may begin between one to several days before both primary and recurrent infections develop. This is called a prodrome. In treating herpes or other viral infections, prodrome may signal when to begin applying the anti-viral zinc containing compositions of the present invention.

Viruses are infectious agents composed of protein, nucleic acids, and in some instances a lipid coating (lipid-capsid viruses). Generally speaking, the anti-viral zinc containing compositions of the present invention are particularly effective against lipid-capsid viruses. The anti-viral zinc containing compositions of the present invention are also particularly effective against viruses that cause commonly associated skin symptoms, such as lesions, rashes, blisters, pimples, redness, tingling sensations, itchiness, burning sensations, and the like. More specifically, the anti-viral zinc containing compositions are effective against one or more of herpes viruses, such as HSV type 1, HSV type 2, acyclovir-resistant HSV type 1, acyclovir-resistant HSV type 2, varicella zoster virus, cytomegalovirus, and papilloma viruses.

The zinc containing compositions contain at least one zinc compound. While not wishing to be bound by any theory, it is believed that the zinc compound (or zinc ion) contributes to the inhibition, inactivation, reaction with, or otherwise interruption of the activity of the target virus.

A zinc compound contains at least one atom of zinc. Zinc compounds include zinc, zinc ions such as divalent zinc ions, zinc salts such as divalent zinc salts, zinc hydrates such as zinc salt hydrates, such as zinc sulfate heptahydrate, and zinc oxides. Zinc salts include inorganic zinc salts and organic zinc salts. Organic zinc salts include zinc carboxylic acid salts, zinc hydroxycarboxylic acid salts, and zinc aminocarboxylic acid salts.

Examples of zinc compounds include zinc, zinc chloride, zinc acetate, zinc citrate, zinc sudoxicam, zinc sulfate, zinc nitrate, zinc carbonate, zinc tartrate, zinc maleate, zinc lactate, zinc aminoacetate, zinc aspartate, zinc glutamate, zinc propionate, zinc oleate, zinc benzoate, zinc gluconate, zinc butyrate, zinc formate, zinc glycerate, zinc glycolate, zinc oxide, zinc ethylenediamine tetraacetate, and hydrates thereof.

In another embodiment, the zinc compound is a zinc complex of polysulfated polysaccharide, such as zinc pentosan polysulfate and the like.

In another embodiment, the zinc compound is zinc oxyacetate. Zinc oxyacetate may be prepared by slowly distilling powdered anhydrous zinc acetate in a high vacuum. Zinc oxyacetate sublimes gradually and is collected as crystalline crust on a cool place in the distillation vessel. Alternatively, zinc oxyacetate can be made by reacting zinc, a carboxylic acid, and hydrogen peroxide in an aqueous mixture and then recovering zinc oxyalkylate as a precipitate.

In one embodiment, the zinc containing compositions contain about 0.005% by weight or more and about 20% by weight or less of at least one zinc compound. In another embodiment, the zinc containing compositions contain about 0.01% by weight or more and about 10% by weight or less of at least one zinc compound. In yet another embodiment, the zinc containing compositions contain about 0.05% by weight or more and about 5% by weight or less of at least one zinc compound. In still yet another embodiment, the zinc containing compositions contain about 0.1% by weight or more and about 2% by weight or less of at least one zinc compound.

The zinc containing compositions contain at least one phenolic antioxidant. The phenolic antioxidant has antioxidant properties and contains a phenol moiety or is derived from a compound containing a phenol moiety. While not wishing to be bound by any theory, it is believed that the phenolic antioxidant contributes to the stability of the composition and/or promotes the destruction of the lipid coating of a target virus (or separates the lipid coating from the nucleic acid sequence of a virus). In this connection, the phenolic antioxidant may act as an active hypolipidemic compound, thereby making the virus more vulnerable to other ingredients and/or the human immune system. The phenolic antioxidant may be liposoluble.

Examples of phenolic antioxidants include butylated hydroxytoluenes (BHTs) including modified BHTs, butylated hydroxyanisoles (BHAs), vitamin E including tocopherols and tocotrienols, and sterically hindered phenolics. The most common BHT is 2,6-di-tert-butyl-4-methylphenol, while the most common BHA is 2(3)-tert-butyl-4-methoxyphenol.

Sterically hindered phenolics are generally obtained by the alkylation of phenol, or a methylene bisphenol, with olefins which may be mixtures such as: isobutylene, alphamethylstyrene, cyclopentene, diisobutylene, nonenes, etc. Specific examples of these phenolic antioxidants are: 2,6-di-tert-butyl-4-methylphenol; 2,6-di-tert-butyl-4-cumylphenol; 2,6-di-tert-butyl-4-nonylphenol; 2,6-dicumylphenol; 2,6-di-tert-butyl-4-isooctylphenol; 4,4'-methylene-bis(2,6-di-tert-butylphenol); and 2,2'-methylene-bis(4-methyl-6-tert-butylphenol).

Modified BHT compounds such as BHT-omega pyridyl ethers may be employed as the phenolic antioxidant compound. Pharmaceutically-active BHT-omega pyridyl ethers are ethers of a BHT-derivative (a butylated hydroxy toluene derivative) and an omega-pyridylalkyl-, -alkenyl-, or -alkinyl-alcohol. More particularly, ether compounds of the Formula I:

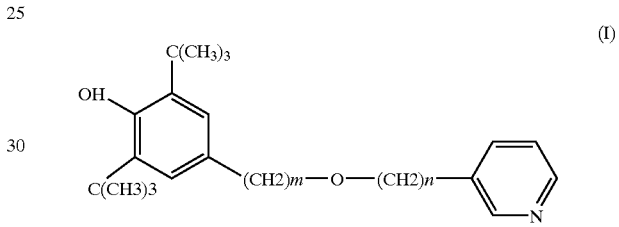

(I)

wherein m=1, 3 wherein $(CH_2)_n$ may optionally include a double bond or a triple bond conjugated to the 3-position of the pyridine ring, that is, the bond between the two carbon atoms of the $(CH_2)_n$ moiety most closely adjacent the pyridine ring may be a single, double, or triple bond, and a pharmaceutically acceptable acid addition salt thereof.

The preparation of the BHT-omega pyridyl ethers can be carried out starting from an omega-pyridylalkyl-, alkenyl-, or alkynyl-alcohol, which is reacted with 3,5-ditert.-butyl-4-hydroxy-benzyl alcohol in the form of its acetate.

The omega-pyridyl-alkyl-alcohol is prepared by a Wittig reaction starting from pyridyl-3-aldehyde and a phosphonium salt, synthesized from the corresponding haloalkylalcohol. The resulting unsaturated omega-pyridyl-alkyl-alcohol is directly, or after hydrogenation, converted into an ether (the modified BHT).

Alternatively, the starting omega-pyridyl-alkyl-alcohol can be prepared by reacting 3-bromopyridine and the corresponding omega-alkynyl alcohol. The resulting omega-pyridylalkynyl-alcohol is converted directly, or after hydrogenation to an omega-pyridyl-alkenyl- or omega-pyridyl-alkyl-alcohol- into the modified BHT. The BHT-omega pyridyl ethers further include acid addition salts of the above compounds.

The compounds of Formula I include specifically the following compounds: 2,6-Di-tert-butyl-4-[8-(3-pyridyl)-2-oxaoctyl]phenol; 2,6-Di-tert-butyl-4-[6-(3-pyridyl)-2-oxahexyl]phenol; 2,6-Di-tert-butyl-4-[7-(3-pyridyl)-2-oxaheptyl]phenol; (Z)-2,6-Di-tert-butyl-4-(8-(3-pyridyl)-2-oxaoct-7-enyl]-phenol; 2,6-Di-tert-butyl-4-[9-(3-pyridyl)-2-oxanonyl]phenol; 2,6-Di-tert-butyl-4-[5-(3-pyridyl)-4-oxapentyl]phenol; 2,6-Di-tert-butyl-4-[7-(3-pyridyl)-4-oxaheptyl]phenol; 2,6-Di-tert-butyl-4-[9-(3-pyridyl)-4- oxanonyl)phenol; and 2,6-Di-tert-butyl-4-[8-(3-pyridyl)-2-oxaoct-7-ynyl]phenol. Specific methods of making these compounds are disclosed in U.S. Pat. No. 5,254,549, which is hereby incorporated by reference.

The compounds having Formula II of the invention contain a group R which is an aliphatic hydrocarbon residue, with or without oxygen, having a linear or branched hydrocarbon chain with $C_1-C_{12}$.

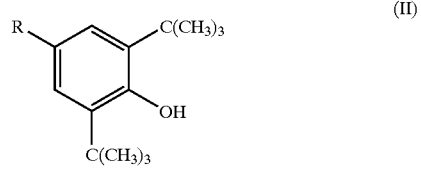

(II)

When R is a non-oxygenated aliphatic residue it may represent an alkyl, alkenyl or alkynyl group having no more than 12 atoms of carbon. $C_1-C_{12}$ include the following: methyl, ethyl, propyl, isopropyl, butyl, isobutyl, s-butyl, t-butyl, amyl, isoamyl, 2,2-dimethylpropyl, n-hexyl, 1,1,3,3-tetramethylbutyl and decyl. C2-C12 alkenyl groups include the following: —CH=CH$_2$, —CH=CHCH$_3$, —CH$_2$CH=CH$_2$, —C(CH$_3$)$_2$CH=CHCH$_3$, —CH=CHCH=CH$_2$, —C(CH$_3$)=CHCH=CH$_2$ and —CH$_3$CH=CHCH$_3$. C2-C12 alkynyl groups include the following: —C≡CH, —CH$_2$C≡CH, —CH$_2$C≡CCH$_3$ and —CH(CH$_3$)C≡CCH$_3$.

When R is an oxygenated aliphatic residue with C1-C12, it may have one or more ether, carbonyl, hydroxyl or carboxyl functions. R groups with C1–C12 alkoxy groups include the following: methyloxy, ethyloxy, propyloxy, isopropyloxy, butyloxy, isobutyloxy, s-butyloxy, t-butyloxy, amyloxy, isoamyloxy, 2,2-dimethylpropyloxy, n-hexyloxy, 1,1,3,3-tetramethylbutyloxy and decyloxy. R groups with C1–C12 carbonyl function (CO) groups include the following: —CHO, —COCH$_3$, —COCH$_2$CH$_3$, —COCH$_2$CH$_2$CH$_3$, —COCH(CH$_3$)$_2$, —COC(CH$_3$)$_3$, —COCH$_2$CH$_2$CH$_2$CH$_3$ and COC(CH$_3$)$_2$CH$_2$(CH$_3$)$_3$. R groups with C1–C12 having a hydroxyl function (OH) include the omega-hydroxylated groups: —CH$_2$OH, —CH$_2$CH$_2$OH, —CH$_2$CH$_2$CH$_2$OH, —C(CH$_3$)$_2$OH, —C(CH$_3$)$_2$CH$_2$OH, —CH$_2$C(CH$_3$)$_2$OH, —CH$_2$C(CH$_3$)$_2$CH$_2$OH, —CH$_2$CH$_2$CH$_2$C(CH$_3$)$_2$CH$_2$OH, —CH$_2$CH(CH$_3$)OH and —C(CH$_3$)$_2$CH$_2$C(CH$_3$)$_2$CH$_2$OH. R groups with C1–C12 having an omega-carboxyl function include —COOH and —A—COOH groups in which A is an aliphatic hydrocarbon residue with C1–C11, such as —COOH, —CH$_2$COOH, —CH(CH$_3$)COOH, —C(CH$_3$)$_2$COOH, —CH$_2$CH$_2$CH$_2$COOH, —CH(CH$_3$)$_2$CH$_2$COOH, —CH=CHCOOH and —C(CH$_3$)=C(CH$_3$)COOH.

Without departing from the scope of the invention, the oxygenated aliphatic group R may have (i) at its end linked to the phenol residue, an ether —O— or carbonyl —CO— function, and (ii) at its other end, an omega —OH or omega —COOH function, with the two ends being linked together by a linear or branched hydrocarbon chain such that the total number of carbon atoms in R is no more than 12.

Salts of the compounds having Formula II, where R is COOH or A—COOH, include the mineral salts obtained by the reaction of the acid having Formula II where R=COOH or A—COOH with a mineral base. These mineral salts are the compounds having Formula II in which R=COOX, where X represents NH$_4$ cation $1/mM^{m+}$, M is a metal from Groups Ia, Ib, IIa and IIb of the periodic table, and m is its valence, notably $N^+$, $K^+$, $1/2Ca^{2+}$, $1/2Zn^{2+}$, $1/2Mg^{2+}$, Cu+ or $1/2Cu^{2+}$.

Addition salts obtained by reacting a compound having Formula II where R=COOH or A—COOH with an organic base, such as the alkylamines and dialkylamines (where each alkyl fragment is a C1–C8 radical with a linear or branched hydrocarbon chain), the N-hydroxyalkylamines in which the alkyl fragment is a divalent C1–C8 radical with a linear or branched hydrocarbon chain, such as 2-hydroxyethylamine); the single-ring saturated or unsaturated cyclic amines (e.g., pyridine, 3-methylpyridine, pyrrolidine, piperidine, 4-methylpiperidine, morpholine, thiomorpholine, piperazine, 4-methylpiperazine, 4-phenylpiperazine, 4-(4-chlorophenyl)piperazine, 4-(2hydroxyethyl)piperazine and hexamethyleneimine), and the amino acids (e.g., Arg, His, Orn, Lys, Gly, Ala, Phe, Glu, Leu, Ile, Nle, Val, Nva, MeGly, Pro, 4Hyp or 3Hyp, where each acid function of the said amino acids is capable of being blocked by a known method of peptide synthesis).

The esters of the acid compounds having Formula II where R is COOH or A—COOH may be represented by the formulae COOZ or A—COOZ, where A is defined as above and Z is a hydrocarbon residue capable of being aminated. Advantageously, Z includes an aliphatic hydrocarbon residue with C1–C5, and the amino group it may contain will be NH$_2$, or one of the following groups: monoalkylamino, dialkylamino, N-hydroxyalkylamino and cyclic amino, as defined in the context of the addition salts above.

Esters of acid components having Formula II where R is COOH or A—COOH, include the alkyl and aminoalkyl esters in which each alkyl fragment is a linear or branched hydrocarbon residue with C1–C5.

Specific examples include 3,5-di-t-butyl-4-hydroxyanisole (a compound of Formula II where R is OCH3); 3,5-di-t-butyl-4-hydroxyphenylmethanol (a compound of Formula II where R is CH$_2$OH); 3,5-di-t-butyl-4-hydroxybenzaldehyde (a compound of Formula II where R is CHO); 3,5-di-t-butyl-4-hydroxybenzoic acid (a compound of Formula II where R is COOH); 2,6-di-t-butylphenol (a compound of Formula II where R is an aliphatic hydrocarbon residue); 2,6-di-t-butylparacresol (a BHT of Formula II in which R is methyl); 2,6-di-t-butyl-4-butylphenol (a BHT of Formula II in which R is n-butyl); 2,4,6-tri-t-butylphenol (a BHT of Formula II in which R is t-butyl); 2,6-di-t-butyl-4-(2,2-dimethylpropyl)phenol (a BHT of Formula II in which R is CH$_2$C(CH$_3$)$_3$); 2,6-di-t-butyl-4-hexylphenol (a BHT of Formula II in which R is n-hexyl); and 2,6-di-t-butyl-4-(1,1,3,3-tetramethylbutyl)phenol (a BHT of Formula II in which R is C(CH$_3$)$_2$CH$_2$C(CH$_3$)$_3$).

In one embodiment, the zinc containing compositions contain about 0.001% by weight or more and about 20% by weight or less of at least one phenolic antioxidant. In another embodiment, the zinc containing compositions contain about 0.005% by weight or more and about 10% by weight or less of at least one phenolic antioxidant. In yet another embodiment, the zinc containing compositions contain about 0.01% by weight or more and about 5% by weight or less of at least one phenolic antioxidant. In still yet another embodiment, the zinc containing compositions contain about 0.1% by weight or more and about 2% by weight or less of at least one phenolic antioxidant.

In one embodiment, the zinc containing compositions contain one phenolic antioxidant. In another embodiment, the zinc containing compositions contain at least two phenolic antioxidants or two phenolic antioxidants.

In one embodiment, the weight ratio of phenolic antioxidant to zinc compound in the zinc containing compositions is from about 0.75:1 to about 4:1. In another embodiment, the weight ratio of phenolic antioxidant to zinc compound in the zinc containing compositions is from about 1:1 to about 3:1. In yet another embodiment, the weight ratio of phenolic antioxidant to zinc compound in the zinc containing compositions is from about 1.25:1 to about 2.5:1. In some instances, compositions with the above-described weight ratios provide particular effectiveness against herpes viruses.

The zinc containing compositions contain at least one analgesic. Analgesics mitigate pain and/or discomfort due to the action of the zinc containing compositions or due to symptoms of the viral infection. Analgesics include analgesic compounds and anesthetic compounds. While not wishing to be bound by any theory, it is believed that the analgesic contributes to the frequent use of anti-viral zinc containing compositions. For example, when mild pain is attributable to the action of the zinc containing compositions, the analgesics mitigate such pain. Also an increase in pain several hours after application generated by viral activity may signal the need for additional applications of the zinc containing compositions to affected areas of a subject.

Examples of analgesics include salicylic type compounds including salicylic acid, acetylsalicylic acid, acetaminophen, aloe compounds such as aloe juice extract and aloe vera, antipyrine (phenazone), benzocaine (ethyl aminobenzoate), bromfenac, fenoprofen, ibuprofen, indomethacin, lidocaine, naproxen, piroxicam, tolmetin, tramadol, and the like.

In one embodiment, the zinc containing compositions contain about 0.1% by weight or more and about 50% by weight or less of at least one analgesic. In another embodiment, the zinc containing compositions contain about 1% by weight or more and about 40% by weight or less of at least one analgesic. In yet another embodiment, the zinc containing compositions contain about 2% by weight or more and about 35% by weight or less of at least one analgesic.

In one embodiment, the zinc containing compositions contain one analgesic. In another embodiment, the zinc containing compositions contain at least two analgesics or two analgesics. In yet another embodiment, the zinc containing compositions contain at least three analgesics or three analgesics.

The zinc containing compositions of the present invention may contain pharmaceutical adjuvants suitable for topical application. In this connection, the zinc containing compositions may be in the form of one or more of tinctures, solutions, creams, ointments, gels, emulsions, and suspensions. Typically, tinctures, solutions, creams, ointments, gels, emulsions, and suspensions contain purified water and other components.

Regardless of the specific nature of the zinc containing composition, the zinc containing compositions of the present invention contain water and a hydrocarbyl containing compound. Water preferably includes purified water. The amount of water in the zinc containing compositions can vary greatly. In one embodiment, the zinc containing compositions contain about 0.1% by weight or more and about 60% by weight or less of water. In another embodiment, the zinc containing compositions contain about 0.5% by weight or more and about 50% by weight or less of water. In yet another embodiment, the zinc containing compositions contain about 1% by weight or more and about 30% by weight or less of water.

As used herein, the term "hydrocarbyl" means that the group being described has predominantly hydrocarbon character within the context of this invention. These include groups that are not only purely hydrocarbon in nature (containing only carbon and hydrogen), but also groups containing substituents or hetero atoms which do not alter the predominantly hydrocarbon character of the group. Such substituents may include halo-, carbonyl-, ester-, ether-, alkoxy- nitro-, etc. These groups also may contain hetero atoms. Suitable hetero atoms will be apparent to those skilled in the art and include, for example, sulfur, nitrogen and particularly oxygen. Therefore, while remaining mostly hydrocarbon in character within the context of this invention, these groups may contain atoms other than carbon present in a chain or ring otherwise composed of carbon atoms provided that they do not adversely affect the anti-viral activity of the zinc containing compositions of the present invention.

In general, no more than about three non-hydrocarbon substituents or hetero atoms, and preferably no more than one, will be present for every five carbon atoms in the hydrocarbyl based groups. The term "hydrocarbyl" includes C2–C60, or C3–C30 alkyl and alkyloxy groups such as t-butyl, t-butoxy, ethoxy, propyloxy, t-amyl, s-butyl, isopropyl, octyl, nonyl, dodecyl and octadecyl. Alternatively the hydrocarbyl group may be derived from a polyolefin, for example polyethylene, polypropylene, polybutylene or a polyolefin copolymer, for example an ethylene/propylene copolymer, preferably derived from a polyisobutene.

The hydrocarbyl containing compound is a compound that contains at least one hydrocarbyl group, or contains at least a hydrocarbyl portion, and typically is one or more of an organic oil, a petroleum based compound, an organic thickener, or an organic emulsifier. General examples include carboxylic acids, fatty acids, fatty alcohols, fatty acid esters (made of a fatty acid and an alcohol or polyol) including triglycerides and glycol esters, polyalcohols (polyols), waxes, and petrolatum.

Fatty acid esters or carboxylic acid esters include compounds represented by Formula III $$R^1COOR^2 \quad (III)$$

wherein $R^1$ and $R^2$ are independently a hydrocarbyl group having from 1 to 50 carbon atoms, such as an alkyl group having from 1 to about 50 carbon atoms, an oxyalkyl group having from 2 to about 50 carbon atoms, an alkenyl group having from 1 to 50 carbon atoms, an ester or ether containing group having from 2 to about 50 carbon atoms, and an aromatic containing group having from 6 to about 50 carbon atoms. The alkyl group, alkenyl group, and oxyalkyl group may be one or more of straight, branched, or cyclic. The fatty acid esters or carboxylic acid esters represented by Formula III are derived from natural sources or can be made from a carboxylic acid ($R^1$ COOH) and an alcohol ($R^2OH$). The carboxylic acid may be monoacid or polyacid and the alcohol may be monoalcohol or a polyhydric alcohol. Examples of fatty acid esters or carboxylic acid esters include ascorbyl myristate, isopropyl myristrate, ascorbyl palmitate, ascorbyl stearate, glyceryl monostearate, tocopheryl acetate, sorbitan monostearate, isopropyl palmitate, tocopheryl propioniate, tocopheryl butyrate, octyl salicylate, octyl methoxycinnamate, glyceryl linoleate, glyceryl linolenate, glyceryl arachidonate, glycerol monostearate, and stearyl lactylate. Fatty acid esters or carboxylic acid esters often act as an emulsifier or as a thickener.

Fatty acid esters include glyceride compounds represented by Formula IV $$CH_2(OOCR^3)CH(OOCR^4)CH_2(OOCR^5) \quad (IV)$$

wherein $R^3$, $R^4$, and $R^5$ are independently H, a hydrocarbyl group having from 1 to 25 carbon atoms, such as an alkyl group having from 1 to about 25 carbon atoms, an oxyalkyl group having from 2 to about 25 carbon atoms, an alkenyl group having from 1 to 25 carbon atoms, and an aromatic containing group having from 6 to about 25 carbon atoms. The alkyl group, alkenyl group, and oxyalkyl group may be one or more of straight, branched, or cyclic. General examples include monoglycerides (wherein two of $R^3$, $R^4$, and $R^5$ are H), diglycerides (wherein one of $R^3$, $R^4$, and $R^5$ is H), and triglycerides (wherein none of $R^3$, $R^4$, and $R^5$ is H). Specific examples include short chain (wherein $R^3$, $R^4$, and $R^5$ are <C8), medium chain (wherein $R^3$, $R^4$, and $R^5$ are C8–C16), and long chain (wherein $R^3$, $R^4$, and $R^5$ are >C16) monoglycerides, diglycerides, and triglycerides. Fatty acid esters can oft en be derived from plant oils including coconut oil, palm oil, peanut oil, corn oil, and the like. Medium chain triglycerides are particularly derived from coconut oil. Glyceride compounds in some instances can act as a dermal transfer agent. In other instances, glyceride compounds can act as an emulsifier.

Fatty acid esters further include salts of fatty acid esters. Examples include sodium stearoyl lactylate and potassium stearoyl lactylate.

Fatty acids include C5–C60 and preferably C8–C22 carboxylic acids (mono-, di- and other polyacids) such as lauric acid, myristic acid, palmitic acid, oleic acid, hypogeic acid, linoleic acid, linolenic acid, elaidic acid, abietic acid, dihydroabietic acid, dehydroabietic acid, tall oil fatty acids, erucic acid, brassidic acid, caprylic acid, pelargonic acid, capric acid, undecylic acid, tridecoic acid, arachidic acid, eicosenoic acid, behenic acid, enicic acid, tetracosanoic acid, stearic acid, and salts thereof. Fatty alcohols include C2–C60 and preferably C5–C22 alcohols such as lauryl alcohol, cetyl alcohol, capryl alcohol, alcohol, cetearyl alcohol, benzyl alcohol, lanolin alcohols, cetostearyl alcohol, and stearyl alcohol. Polyalcohols include propylene glycol, ethylene glycol, butylene glycol, sorbitol, glycerin, polyethylene glycols, and polypropylene glycols.

Waxes and petrolatum are hydrocarbon compounds and include liquid waxes, solid waxes, petroleum jelly (petrolatum), paraffin oil and/or hard paraffins, which may contain preferably hydroxy compounds suitable for improving the water-absorption, wool wax alcohol, wool wax, candelilla wax, ceresine wax, carnauba wax, polawax, and bees-wax. Waxes and petrolatum often act as a thickener.

Organic oils include mineral oil, essential oils, and fatty vegetable oils. Examples of organic oils include jojoba oil, soya oil, sesame oil, groundnut oil, sunflower oil, olive oil, palm oil, palm kernel oil, castor oil, cocoa oil, coconut oil, corn oil, canola oil, almond oil, wheatgerm oil, rosemary oil, lavender oil, balm mint oil, sage oil, garlic oil, juniper berry oil, aniseed oil, rice bran oil, hemp seed oil, grapeseed oil, safflower oil, spearmint oil, cardamon oil, pimento oil, aniseed oil, rose oil, true rose oil, true Melissa oil, feverfew extract, germanium extract, caraway oil, lemon oil, orange oil, peppermint oil, camphor oil, clove oil, pine-needle oil, eucalyptus oil, Vegelatum® available from Natunola Health Inc., and the like. Oils generally can often act as an emulsifying agent, and some oils can exhibit anti-viral and/or antimicrobial activity. In some embodiments, the zinc containing compositions contain one or more organic oils and petrolatum. In other embodiments, the zinc containing compositions contain one or more organic oils but no petrolatum.

Examples of organic thickeners which may be used in the preparation of the peroxide gel component optionally in combination with one or more inorganic thickeners include natural and synthetic gums such as carrageenan (Irish moss), powdered cellulose, acacia (also called gum arabic), agar, alginic acid and its salts (such as sodium alginate), gum tragacanth, xanthan gum, lanolin (an exudate secreted by sheep into wool fibers), gelatin (a mixture containing collagen, a protein), carboxypolymethylene, glyceryl monostearate, polyacrylamide, sodium carboxymethyl cellulose, starch, polyvinylpyrrolidone, hydroxyethylpropylcellulose, hydroxybutyl methyl cellulose, hydroxypropyl methyl cellulose, hydroxyethyl cellulose, and carboxyvinyl polymers and partially neutralized carboxyvinyl polymers.

The amount of hydrocarbyl containing compound in the zinc containing compositions can also vary greatly. In one embodiment, the zinc containing compositions contain about 5% by weight or more and about 80% by weight or less of at least one hydrocarbyl containing compound. In another embodiment, the zinc containing compositions contain about 10% by weight or more and about 70% by weight or less of at least one hydrocarbyl containing compound. In yet another embodiment, the zinc containing compositions contain about 15% by weight or more and about 65% by weight or less of at least one hydrocarbyl containing compound.

In one embodiment, the zinc containing compositions contain one hydrocarbyl containing compound. In another embodiment, the zinc containing compositions contain at least two hydrocarbyl containing compounds or two hydrocarbyl containing compounds. In yet another embodiment, the zinc containing compositions contain at least three hydrocarbyl containing compounds or three hydrocarbyl containing compounds. In still yet another embodiment, the zinc containing compositions contain at least four hydrocarbyl containing compounds or four hydrocarbyl containing compounds.

Tinctures and solutions generally contain an aqueous ethanolic base, at least one polyalcohol and/or lower polyethylene glycols, optionally a humectant for reducing water loss, and optionally fat-restoring substances, such as fatty acid esters of lower polyethylene glycols polypropylene glycols, including polyoxyethylene sorbitan fatty acid esters, such as polyoxyethylene sorbitan monolaurate or polyoxyethylene sorbitan monooleate.

Creams are oil-in-water emulsions which contain more than about 50% of water (purified water). Fatty alcohols may be used as an oleaginous base, alternatively or additionally fatty acids, liquid to solid waxes, for example isopropyl myristinate, wool wax or bees-wax, and/or hydrocarbons may be used. Suitable emulsifiers are surface-active substances with primarily hydrophilic properties, such as corresponding non-ionic emulsifiers, for example fatty acid esters of polyalcohols or ethylene oxide adducts thereof, such as polyglycerin fatty acid esters or polyoxyethylene sorbitan fatty acid esters (Tweens); polyoxyethylene fatty alcohol ethers or esters; or corresponding ionic emulsifiers, such as alkali metal salts of fatty alcohol sulfates, for example sodium lauryl sulphate, sodium cetyl sulphate or sodium stearyl sulphate, which are customarily used in the presence of fatty alcohols. Additives to the water phase include agents which reduce water less through evaporation, for example polyalcohols, such as glycerin, sorbitol, propylene glycol and/or polyethylene glycols.

Ointments are water-in-oil emulsions which contain up to about 70%, but typically from about 10% to about 50% by weight, of water or aqueous phase. The oleaginous phase comprises chiefly hydrocarbons, for example petrolatum, paraffin oil and/or hard paraffins, which may contain hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters, for example sorbitan oleate and/or sorbitan isostearate. Optional additives to the water phase include humectants, such as polyalcohols.

Gels are aqueous solutions of the active substances in which gel formers, such as those of the group of cellulose ethers, for example methyl cellulose, hydroxyethyl cellulose or carboxymethyl cellulose, or of the vegetable hydrocolloids, such as sodium alginate, tragacanth or gum arabic, are dispersed and swelled. The gels optionally also contain humectants from the group of the polyalcohols and/or wetting agents, for example polyoxyethylene sorbitan fatty acid esters, such as polyoxyethylene sorbitan monostearate, monolaurate or monooleate, in concentrations from about 0.02% to about 5%. As further adjuvants, the gels may contain conventional preservatives, for example benzyl alcohol, phenethyl alcohol, phenoxyethanol, lower alkyl esters of p-hydroxybenzoic acid such as the methyl and/or propyl esters, sorbic acid or organic mercury compounds such as merthiolate.

In suspensions and emulsions, additives that are often used to prevent insoluble particles or immiscible droplets from coalescing, settling to the bottom, or floating to the surface. In soluble gels, such agents are used to thicken the mixture and help ensure that all of the molecular components remain in a stable suspended condition and do not separate into layers based on density differences. Such additives may be termed suspending agents or thickening agents.

The zinc containing compositions of the present invention may optionally contain one or more lubricating agents. Lubricating agents include glycerin (including glycerine, glycerol, 1,2,3-propanetriol, and trihydroxypropane) and certain types of polyethylene glycol (PEG), such as PEG 200 or PEG 400, polypropylene glycol, polyisobutene, polyoxyethylenes, behenic acid, behenyl alcohol, sugar-alcohols such as sorbitol, and silicon compounds such as polydimethylsiloxane.

Other optional additives include preservatives (such as chlorhexidine gluconate), anti-inflammatory compounds, anti-crystallization agents (such as glucono-delta-lactate), fragrances, coloring agents, alkaline or acidic agents to maintain a desired pH, skin conditioning agents, and soothing or anti-swelling agents such as lanolin, or hydrocortisone. Skin conditioning agents include glycerin, propylene glycol, sorbitol, lanolin, lanolin derivatives, acyl lactylates, polyethylene glycol, allantoine, alginates, monoester salts of sulfosuccinates, alphahydroxy fatty acids, ceramides, and mixtures thereof.

Many cosmetics, shampoos, and other topically applied mixtures contain alcohols, detergents, or other chemicals that would irritate the skin if applied in concentrated form, but which are acceptable in low concentration, especially if any irritating effects are suppressed or masked by soothing or anti-swelling agents. Accordingly, the zinc containing compositions may contain a relatively small quantity of compounds (including anti-viral agents) that might be irritants if present in concentrated form, provided that the resultant composition does not cause substantial irritation (a relatively small quantity to mitigate irritation).

Inorganic thickeners may also be included the zinc containing compositions. Examples of particulated inorganic compounds useful in thickening the zinc containing compositions include inorganic thickeners such as fumed silicas, clays such as Laponite, bentonite, kaolin, and the like, amorphous silicas, alumina and mica. The particulated water insoluble inorganic compounds may be incorporated in the zinc containing compositions in an amount from about 0.05% to about 5% by weight, or from about 0.1% to about 1% by weight.

In addition to containing the conventional preservatives, the zinc containing compositions of the present invention may contain additional active compounds, for example antiphlogistics or antimicrobials, such as antibacterials, antifungals or additional anti-virals. Additional anti-virals include, for example flumethasone, neomycin, gentamycin, lactic acid or mikonazole.

The zinc containing compositions are made by simply mixing the ingredients. The order in which the ingredients are added together is not critical to the invention. Generally however, the zinc compound is combined with water while the phenolic antioxidant is combined with a hydrocarbyl containing compound. Other organic components may be combined with the phenolic antioxidant and hydrocarbyl containing compound (organic phase) while water-soluble optional components can be combined with the zinc compound and water (aqueous phase). The organic and aqueous phases may be mixed together to form the zinc containing compositions. Alternatively, all ingredients may be together within a short period of time. The combined composition may be heated, whereby one or both of the aqueous and organic phase components may be removed.

The zinc containing compositions are applied to a subject by contacting the zinc containing compositions with skin and/or mucous membranes. A thin film of the zinc containing composition is formed by gently rubbing and spreading the composition across skin and/or mucous membranes. In one embodiment, the thickness of film may vary from about 0.1 $\mu$m to about 1 mm. In another embodiment, the thickness of film may vary from about 1 $\mu$m to about 0.5 mm. Since a portion of the zinc containing composition may be absorbed by skin and/or mucous membranes, the lower limit of the thickness range may further vary beyond the ranges provided. The zinc containing compositions may be applied as often as necessary to prevent viral induced lesions/breakouts, such as every few hours.

Another aspect of the present invention is the application of zinc containing compositions to a subject while the subject is on a low arginine diet. A low arginine diet involves avoiding foods and beverages containing relatively large amounts of arginine, or avoiding foods and beverages that upon digestion, lead to the production of relatively large amounts of arginine. Combining a low arginine diet with the application of the zinc containing compositions of the present invention serves to further inhibit the occurrences of viral induced lesions/breakouts. Foods high in arginine are chocolate, gelatine, peanuts, seeds and nuts.

Yet another aspect of the present invention is the application of zinc containing compositions to a subject while the subject is on a high lysine diet. A high lysine diet involves consuming foods and beverages containing relatively large amounts of lysine, or consuming foods and beverages that upon digestion, lead to the production of relatively large amounts of lysine. Combining a high lysine diet with the application of the zinc containing compositions of the present invention serves to further inhibit the occurrences of viral induced lesions/breakouts. Foods high in lysine are vegetables, fish, turkey and chicken, star fruit, papaya, grapefruit, apricot, pear, apple, fig, black beans, lentils, soybeans, and dairy products. Lysine supplements also provide high levels of lysine.

The following examples illustrate the present invention. Unless otherwise indicated in the following examples and

EXAMPLE 1

An emulsion is prepared by combining 0.3% zinc sulfate heptahydrate, 10% purified water, 18% medium chain triglyceride oil, 30% petrolatum, 5% bees-wax, 0.6% BHT, 0.1% vitamin E, 4% sodium stearoyl lactylate, 4% glyceryl monostearate, 20% aloe vera extract, and 8% benzocaine.

EXAMPLE 2

A thick emulsion is prepared by combining 0.3% zinc sulfate heptahydrate, 10% purified water, 18% medium chain triglyceride oil, 23% petrolatum, 5% bees-wax, 0.6% BHT, 0.1% vitamin E, 4% sodium stearoyl lactylate, 4% glyceryl monostearate, 20% aloe vera extract, and 15% benzocaine.

EXAMPLE 3

An emulsion is prepared by combining 0.3% zinc sulfate heptahydrate, 18% purified water, 18% medium chain triglyceride oil, 26% petrolatum, 5% bees-wax, 0.7% BHT, 4% sodium stearoyl lactylate, 4% glyceryl monostearate, 20% aloe vera extract, and 4% benzocaine.

EXAMPLE 4

An emulsion is prepared by combining 0.5% zinc sulfate heptahydrate, 17% purified water, 20% medium chain triglyceride oil, 20% petrolatum, 10% bees-wax, 3% BHT, 4.5% sodium stearoyl lactylate, 4.5% glyceryl monostearate, and 20.5% aloe vera extract.

EXAMPLE 5

An emulsion is prepared by combining 0.5% zinc sulfate heptahydrate, 20% purified water, 30% medium chain triglyceride oil, 10% petrolatum, 5% bees-wax, 5% BHT, 4.5% sodium stearoyl lactylate, 4.5% glyceryl monostearate, and 20.5% aloe vera extract.

EXAMPLE 6

An emulsion is prepared by combining 0.5% zinc sulfate heptahydrate, 20% purified water, 28% medium chain triglyceride oil, 10% petrolatum, 5% bees-wax, 5% BHT, 2% vitamin E, 4.5% sodium stearoyl lactylate, 4.5% glyceryl monostearate, and 20.5% aloe vera extract.

EXAMPLE 7

An emulsion is prepared by combining 0.3% zinc sulfate heptahydrate, 10% purified water, 18% medium chain triglyceride oil, 30% petrolatum, 5% bees-wax, 0.6% BHT, 0.1% vitamin E, 4% sodium stearoyl lactylate, 4% glyceryl monostearate, 20% aloe vera extract, and 8% benzocaine. The emulsion is heated to about 120° F. where separation between the aqueous and organic phase occurs. The aqueous phase is removed from the composition.

EXAMPLE 8

An emulsion is prepared by combining 0.3% zinc sulfate heptahydrate, 15% purified water, 18% medium chain triglyceride oil, 23% petrolatum, 0.6% BHT, 0.1% vitamin E, 4% sodium stearoyl lactylate, 4% glyceryl monostearate, 20% aloe vera extract, and 15% benzocaine.

EXAMPLE 9

A mixture is prepared by combining 2% zinc aspartate, 15% purified water, 20% medium chain triglyceride oil, 3% true Melissa oil, 27% petrolatum, 10% BHA, and 23% salicylic acid.

EXAMPLE 10

A mixture is prepared by combining 5% zinc oleate, 20% purified water, 20% propylene glycol, 8% BHA, 17% isopropyl myristate, 10% propylene glycol monostearate, 5% silica, and 15% acetylsalicylic acid.

EXAMPLE 11

A mixture is prepared by combining 9% zinc benzoate, 30% purified water, 11% glycerine, 20% paraffin, 0.9% BHT, 1.1% tocotrienols, 5% stearyl alcohol, 5% glyceryl monostearate, and 18% aloe vera extract.

EXAMPLE 12

An emulsion is prepared by combining 0.3% zinc acetate, 22% purified water, 18% mineral oil, 5% bees-wax, 0.1% BHT, 0.9% tocotrienols, 4% magnesium stearate, 4.7% isopropyl myristate, 25% petrolatum, 15% aloe vera extract, and 5% benzocaine.

EXAMPLE 13

An emulsion is prepared by combining 1% zinc lactate, 25% purified water, 20% medium chain triglyceride oil, 20% petrolatum, 1% BHT, 13% propylene glycol monostearate, 11% aloe vera extract, and 9% benzocaine.

The compositions of Examples 1 to 6 are applied to herpes induced outbreaks on the genitalia of a designated number of subjects, as reported in Table 1. In particular, the compositions are simply spread over the effected area, for example using a sterile instrument or Q-tip. Table 1 reports the average time to shutdown (shutdown meaning a substantial and/or complete remission of a blisterous herpes outbreak) for the subjects. A complete shutdown involves an end to the viral activity that induced the outbreak. A substantial shutdown means that some residual redness and/or minor tingling may persist, but viral activity is inhibited.

TABLE 1

| Example # | Subjects | Time to Shutdown |
| --- | --- | --- |
| 1 | 3 | 24 hours |
| 2 | 3 | 24 hours |
| 3 | 1 | 24 hours |
| 4 | 3 | 48 hours |
| 5 | 3 | 48 hours |
| 6 | 3 | 48 hours |
| 7 | 1 | 24 hours |

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A zinc containing anti-viral composition, comprising:
   about 0.005% by weight or more and about 20% by weight or less of at least one zinc compound;
   about 0.001% by weight or more and about 20% by weight or less of at least one antioxidant selected from the group consisting of butylated hydroxytoluene; 2(3)-tert-butyl-4-methoxyphenol; 2,6-di-tert-butyl-4-cumylphenol; 2,6-di-tert-butyl-4-nonylphenol; 2,6-dicumylphenol; 2,6-di-tert-butyl-4-isooctylphenol; 4,4'-methylene-bis(2,6-di-tert-butylphenol); and 2,2'-methylene-bis(4-methyl-6-tert-butylphenol);

about 0.1% by weight or more and about 50% by weight or less of at least one analgesic;

about 5% by weight or more and about 80% by weight or less of at least one hydrocarbyl containing compound; and about 0 1% by weight or more and about 60% by weight or less of water.

2. The zinc containing anti-viral composition of claim 1, wherein the zinc compound comprises at least one selected from the group consisting of zinc, zinc chloride, zinc acetate, zinc citrate, zinc sudoxicam, zinc sulfate, zinc nitrate, zinc carbonate, zinc tartrate, zinc maleate, zinc lactate, zinc aminoacetate, zinc aspartate, zinc glutamate, zinc propionate, zinc oleate, zinc benzoate, zinc gluconate, zinc butyrate, zinc formate, zinc glycerate, zinc glycolate, zinc oxide, zinc ethylenediamine tetraacetate, zinc pentosan polysulfate, zinc oxyacetate, and hydrates thereof.

3. The zinc containing anti-viral composition of claim 1, wherein the butylated hydroxytoluene comprises at least one selected from the group consisting of 2,6-di-tert-butyl-4-methylphenol and 2,2'-methylene-bis(4-methyl-6-tert-butylphenol).

4. The zinc containing anti-viral composition of claim 1, wherein the analgesic comprises at least one selected from the group consisting of salicylic acid, acetylsalicylic acid, acetaminophen, an aloe compound, antipyrine, benzocaine, bromfenac, fenoprofen, ibuprofen, indomethacin, lidocaine, naproxen, piroxicam, tolmetin, and tramadol.

5. The zinc containing anti-viral composition of claim 1, wherein the at least one hydrocarbyl containing compound comprises at least two selected from the group consisting of an organic oil, a petroleum based compound, an organic thickener, and an organic emulsifier.

6. The zinc containing anti-viral composition of claim 1, wherein the at least one hydrocarbyl containing compound comprises at least two selected from the group consisting of a wax, petrolatum, a carboxylic acid ester, a fatty acid, and a fatty alcohol.

7. The zinc containing anti-viral composition of claim 1, wherein a weight ratio of the antioxidant to the zinc compound is from about 0.75:1 to about 4:1.

8. A method of treating lesionous symptoms of a viral infection, comprising:

applying an effective amount of a zinc containing composition to the lesions, the zinc containing composition comprising about 0.005% by weight or more and about 20% by weight or less of at least one zinc compound, about 0.001% by weight or more and about 20% by weight or less of at least one antioxidant selected from the group consisting of butylated hydroxytoluene; 2(3)-tert-butyl-4-methoxyphenol; 2,6-di-tert-butyl-4-cumylphenol; 2,6-di-tert-butyl-4-nonylphenol; 2,6-dicumylphenol; 2,6-di-tert-butyl-4-isooctylphenol; 4,4'-methylene-bis(2,6-di-tert-butylphenol); and 2,2'-methylene-bis(4-methyl-6-tert-butylphenol), about 0.1% by weight or more and about 50% by weight or less of at least one analgesic, about 5% by weight or more and about 80% by weight or less of at least one hydrocarbyl containing compound, and about 0.1% by weight or more and about 60% by weight or less of water.

9. The method of claim 8, wherein the zinc containing composition is applied to lesions on skin or to lesions on mucous membranes.

10. The method of claim 8, wherein the zinc compound comprises at least one selected from the group consisting of zinc acetate, zinc citrate, zinc sulfate, zinc nitrate, zinc carbonate, zinc tartrate, zinc maleate, zinc lactate, zinc oleate, zinc benzoate, zinc glycerate, zinc glycolate, zinc oxyacetate, and hydrates thereof.

11. The method of claim 8, wherein the butylated hydroxytoluene comprises at least one selected from the group consisting of 2,6-di-tert-butyl-4-methylphenol and 2,2'-methylene-bis(4-methyl-6-tert-butylphenol).

12. The method of claim 8, wherein the hydrocarbyl containing compound comprises at least one carboxylic acid ester.

13. The method of claim 8, wherein the effective amount of the zinc containing composition is applied by forming a film over the lesions having a thickness from about 0.1 $\mu$m to about 1 mm.

14. The method of claim 8, further comprising adhering to a low arginine diet.

15. The method of claim 8, wherein a weight ratio of the antioxidant to the zinc compound is from about 0.75:1 to about 4:1.

16. A method for the topical treatment of herpes infections in humans, comprising applying to an area of skin or mucous membrane infected with herpes an effective amount of a zinc containing composition comprising about 0.01% by weight or more and about 10% by weight or less of at least one zinc salt, about 0.005% by weight or more and about 10% by weight or less of at least one antioxidant selected from the group consisting of butylated hydroxytoluene; 2(3)-tert-butyl-4-methoxyphenol; 2,6-di-tert-butyl-4-cumylphenol; 2,6-di-tert-butyl-4-nonylphenol; 2,6-dicumylphenol; 2,6-di-tert-butyl-4-isooctylphenol; 4,4'-methylene-bis(2,6-di-tert-butylphenol); and 2,2'-methylene-bis(4-methyl-6-tert-butylphenol), about 1% by weight or more and about 40% by weight or less of at least one analgesic, about 5% by weight or more and about 80% by weight or less of at least two hydrocarbyl containing compounds, and about 0.1% by weight or more and about 60% by weight or less of water.

17. The method of claim 16, wherein the zinc containing composition is applied to a lesionous area of skin or mucous membrane.

18. The method of claim 16, wherein the butylated hydroxytoluene comprises at least one selected from the group consisting of 2,6-di-tert-butyl-4-methylphenol and 2,2'-methylene-bis(4-methyl-6-tert-butylphenol).

19. The method of claim 16, wherein a weight ratio of the antioxidant to the zinc salt is from about 1:1 to about 3:1.

20. The method of claim 16, further comprising adhering to a low arginine diet and a high lysine diet.

21. A method of treating lesionous symptoms of a viral infection, comprising:

applying an effective amount of a zinc containing composition to the lesions, the zinc containing composition comprising about 0.005% by weight or more and about 20% by weight or less of at least one zinc compound, about 0.001% by weight or more and about 20% by weight or less of at least one phenolic antioxidant, about 0.1% by weight or more and about 50% by weight or less of at least one analgesic, about 5% by weight or more and about 80% by weight or less of at least one hydrocarbyl containing compound, and about 0.1% by weight or more and about 60% by weight or less of water; and adhering to a low arginine diet.

22. A method for the topical treatment of herpes infections in humans, comprising:

applying to an area of skin or mucous membrane infected with herpes an effective amount of a zinc containing composition comprising about 0.01% by weight or more and about 10% by weight or less of at least one zinc salt, about 0.005% by weight or more and about 10% by weight or less of at least one phenolic antioxidant, about 1% by weight or more and about 40% by weight or less of at least one analgesic, about 5% by weight or more and about 80% by weight or less of at least two hydrocarbyl containing compounds, and about 0.1% by weight or more and about 60% by weight or less of water; and adhering to a low arginine diet and a high lysine diet.

* * * * *

UNITED STATES PATENT AND TRADEMARK OFFICE
CERTIFICATE OF CORRECTION

PATENT NO.     : 6,475,526 B1
DATED          : November 5, 2002
INVENTOR(S)    : Jeffrey B. Smith It is certified that error appears in the above-identified patent and that said Letters Patent is hereby corrected as shown below:

Column 15,
Line 12, please change the figure number from "0 1%" to -- 0.1% --.

Signed and Sealed this

Twenty-fifth Day of March, 2003

JAMES E. ROGAN
*Director of the United States Patent and Trademark Office*